(12) United States Patent
Davenport et al.

(10) Patent No.: US 8,920,409 B2
(45) Date of Patent: Dec. 30, 2014

(54) SYSTEM AND METHOD FOR DERMATOLOGICAL LESION TREATMENT USING GAS DISCHARGE LAMP WITH CONTROLLABLE CURRENT DENSITY

(75) Inventors: Scott A. Davenport, Half Moon Bay, CA (US); David A. Gollnick, San Francisco, CA (US)

(73) Assignee: Cutera, Inc., Brisbane, CA (US)

( * ) Notice: Subject to any disclaimer, the term of this patent is extended or adjusted under 35 U.S.C. 154(b) by 1457 days.

(21) Appl. No.: 12/286,655

(22) Filed: Oct. 1, 2008

(65) Prior Publication Data
US 2009/0093799 A1    Apr. 9, 2009

Related U.S. Application Data

(60) Provisional application No. 60/977,609, filed on Oct. 4, 2007.

(51) Int. Cl.
*A61N 5/06* (2006.01)
*A61B 18/20* (2006.01)
*A61B 18/00* (2006.01)

(52) U.S. Cl.
CPC ............ *A61N 5/0616* (2013.01); *A61B 18/203* (2013.01); *A61B 2018/00452* (2013.01); *A61B 2018/00458* (2013.01); *A61N 2005/0654* (2013.01); *A61N 2005/0661* (2013.01)
USPC ................................................ 606/9; 607/90

(58) Field of Classification Search
None
See application file for complete search history.

(56) References Cited

U.S. PATENT DOCUMENTS

| | | | |
|---|---|---|---|
| 4,298,005 A | 11/1981 | Mutzhas | 128/396 |
| 5,000,752 A | 3/1991 | Hoskin et al. | 606/9 |
| 5,057,104 A | 10/1991 | Chess | 606/9 |
| 5,074,861 A | 12/1991 | Schneider et al. | 606/17 |
| 5,217,455 A | 6/1993 | Tan | 606/9 |
| 5,282,797 A | 2/1994 | Chess | 606/9 |
| 5,282,842 A | 2/1994 | Changaris | 607/88 |
| 5,290,273 A | 3/1994 | Tan | 606/9 |
| 5,312,395 A | 5/1994 | Tan et al. | 606/9 |
| 5,320,618 A | 6/1994 | Gustafsson | 606/9 |

(Continued)

FOREIGN PATENT DOCUMENTS

| | | | |
|---|---|---|---|
| DE | 003347730 A1 | 7/1985 | A61N 5/06 |
| FR | 1139096 | 6/1957 | |

(Continued)

OTHER PUBLICATIONS

Brochure by Palomar EsteLux™, "Pulsed-Light System," website http://www.palmed.com/laser_estelux.html, printed Jul. 15, 2003, 3 pages in length.

(Continued)

*Primary Examiner* — Lynsey Crandall
(74) *Attorney, Agent, or Firm* — Morrison & Foerster LLP

(57) ABSTRACT

A device for treatment of dermatological lesions includes a gas discharge lamp for generating a plurality of different electromagnetic radiation treatments. A power supply for driving the gas discharge lamp is selectively controlled to drive the gas discharge lamp to output a first electromagnetic treatment when an area of skin being treated has a pigmented lesion, and to drive the gas discharge lamp to output a second electromagnetic treatment when the area of skin being treated has a vascular lesion, where the second electromagnetic treatment has a spectral distribution that is blue-shifted relative to the spectral distribution of the first electromagnetic treatment.

4 Claims, 12 Drawing Sheets

(56) References Cited

U.S. PATENT DOCUMENTS

| | | | |
|---|---|---|---|
| 5,344,418 A * | 9/1994 | Ghaffari | 606/9 |
| 5,405,368 A | 4/1995 | Eckhouse | 607/88 |
| 5,595,568 A * | 1/1997 | Anderson et al. | 606/9 |
| 5,620,478 A | 4/1997 | Eckhouse | 607/88 |
| 5,626,631 A | 5/1997 | Eckhouse | 607/88 |
| 5,643,334 A | 7/1997 | Eckhouse et al. | 607/88 |
| 5,658,323 A | 8/1997 | Miller | 607/89 |
| 5,683,380 A | 11/1997 | Eckhouse et al. | 606/9 |
| 5,720,772 A | 2/1998 | Eckhouse | 607/88 |
| 5,735,844 A | 4/1998 | Anderson et al. | 606/9 |
| 5,755,751 A | 5/1998 | Eckhouse | 607/88 |
| 5,776,175 A | 7/1998 | Eckhouse et al. | 607/100 |
| 5,828,803 A | 10/1998 | Eckhouse | 385/88 |
| 5,830,208 A | 11/1998 | Muller | 606/9 |
| 5,836,999 A | 11/1998 | Eckhouse et al. | 607/88 |
| 5,849,029 A | 12/1998 | Eckhouse et al. | 607/104 |
| 5,885,273 A | 3/1999 | Eckhouse et al. | 606/9 |
| 5,964,749 A | 10/1999 | Eckhouse et al. | 606/9 |
| 5,968,034 A | 10/1999 | Fullmer et al. | 606/9 |
| 6,059,820 A | 5/2000 | Baronov | 607/89 |
| 6,080,147 A | 6/2000 | Tobinick | 606/9 |
| 6,159,204 A | 12/2000 | Hibst | 606/10 |
| 6,174,325 B1 | 1/2001 | Eckhouse | 607/88 |
| 6,193,711 B1 | 2/2001 | Connors et al. | 606/12 |
| 6,214,034 B1 | 4/2001 | Azar | 607/89 |
| 6,273,883 B1 | 8/2001 | Furumoto | 606/9 |
| 6,280,438 B1 | 8/2001 | Eckhouse et al. | 606/9 |
| 6,324,078 B1 | 11/2001 | Naruo et al. | 363/17 |
| 6,383,176 B1 | 5/2002 | Connors et al. | 606/9 |
| 6,514,243 B1 | 2/2003 | Eckhouse et al. | 606/9 |
| 6,595,986 B2 | 7/2003 | Almeida | 606/9 |
| 6,632,219 B1 | 10/2003 | Baranov et al. | 606/9 |
| 6,663,659 B2 | 12/2003 | McDaniel | 607/88 |
| 6,897,238 B2 | 5/2005 | Anderson | 514/563 |
| 7,291,140 B2 | 11/2007 | MacFarland et al. | 606/9 |
| 2002/0019625 A1 | 2/2002 | Azar | 606/9 |
| 2003/0069567 A1 | 4/2003 | Eckhouse et al. | 606/9 |
| 2004/0010298 A1 | 1/2004 | Altshuler et al. | 607/88 |
| 2004/0147985 A1 | 7/2004 | MacFarland et al. | 607/90 |
| 2005/0107850 A1 | 5/2005 | Vaynberg et al. | 607/88 |
| 2005/0177141 A1 * | 8/2005 | Davenport et al. | 606/9 |
| 2006/0052847 A1 | 3/2006 | Davenport et al. | 607/88 |
| 2007/0255265 A1 * | 11/2007 | Davenport et al. | 606/9 |

FOREIGN PATENT DOCUMENTS

| | | | |
|---|---|---|---|
| FR | 2 639 834 | 6/1990 | A61N 1/40 |
| JP | H2/86565 | 7/1990 | A61N 5/06 |
| JP | H4/53569 | 2/1992 | A61N 5/06 |
| SU | 1130354 | 12/1984 | A61N 5/06 |
| WO | WO 91/15264 | 10/1991 | A61N 5/06 |

OTHER PUBLICATIONS

Brochure by Lumenis Aesthetic, "VascuLight™ The World's Most Versatile System for Aesthetic Procedures," website http://www.aesthetic.lumenis.com/wt/content/vasculaight, printed Jul. 15, 2003, 2 pages in length.

Brochure by Lumenis, "VASCU*Light*™ Elite [Versatility and Speed for the Ultimate Aesthetic System]," Copyright 2002, the Lumenis group of companies, 2 pages in length.

Brochure by Lumenis, "VASCU*Light*™ VS [Versatility and Speed for the Ultimate Aesthetic System]," Copyright 2002, the Lumenis group of companies, 2 pages in length.

Brochure by Lumenis, "VASCU*Light*™ SR [Versatility and Speed for the Ultimate Aesthetic System]," Copyright 2002, the Lumenis group of companies, 2 pages in length.

C. Chess et al., "Cool Laser Optics Treatment of Large Telangiectasia of the Lower Extremities," *J. Dermatol. Surg. Oncol.*, vol. 19, pp. 74-80 (1993).

J.S. Dover et al., "Pigmented Guinea Pig Skin Irradiated With Q-Switched Ruby Laser Pulses," *Arch. Dermatol.*, vol. 125, Jan. 1989, pp. 43-49.

"Laser Surgery of Angiomas with Special Reference to Port-Wine Angiomas,"*AMA Association*, Jun. 18-22, 1967, 8 pages in length.

T. Ohshiro et al., "The Ruby and Argon Lasers in the Treatment of Naevi," *Annals Academy of Medicine*, vol. 12, No. 2 (Suppl.), Apr. 1983, 8 pages in length.

T. Ohshiro, "Treatment by Ruby Laser Beams in the Field of Dermatology," "*Japan Medical News*," Separate vol. No. 2768, issued on May 14, 1997, 21 pages in length (English translation attached).

H. Ohtsuka et al., "Ru Laser Histological Studies and Clinical Experiences of Ruby Laser Treatment," 9 pages in length (1991) (1st page is an English Abstract).

L.L. Polla et al., "Melanosomes Are a Primary Target of Q-Switched Ruby Laser Irradiation in Guinea Pig Skin," *The Journal of Investigative Dermatology*, vol. 89, No. 3, Sep. 1987, pp. 281-286.

R.M. Adrian, "Treatment of Facial Telangiectasia Using the VersaPulse® Variable Pulse Width Frequency Doubled Neodymium:YAG Laser: A Case Report," 2 pages in length.

A.K. Alimov et al., "Light/Therapy Irradiating Unit," *Geliotekhnika*, vol. 27, No. 2, pp. 67-68, (1991).

A.K. Alimov et al., "Universal Therapeutic Irradiator," *Geliotekhnika*, vol. 28, No. 4, pp. 74-76, (1992).

D. Berger, "Simulating Solar UV, Accurate Simulation of Ultraviolet Solar Radiation Helps Speed Sunscreen Development," 4 pages in length. (In existence as of Dec. 2002).

P. Bjerring et al., "Intense Pulsed Light Source for Treatment of Small Melanocytic Nevi and Solar Lentigines," *Journal of Cutaneous Laser Therapy*, vol. 2, pp. 177-181, (2000).

B.L. Diffey, "The Spectral Emissions from Ultraviolet Radiation Lamps Used in Dermatology," *Photodermatology*, vol. 3, pp. 179-185, (1986).

R. Fitzpatrick et al., "Treatment of Leg Veins: A Comparison of Laser Therapy with a Noncoherent, Multiwave Light Source," pp. 238-239. (In existence as of Dec. 31, 2002).

R.W. Gange et al., "Cutaneous Photosensitization by 8/Methoxypsoralen: Order/Dependent Synergism Between Radiation > 380 nm and Broadband UVA," *The Journal of Investigative Dermatology*, vol. 82, No. 6, pp. 594-597, (1984).

F. Jacka et al., "A Lamp for Cancer Phototherapy," *Aust. J. Phys.*, vol. 36, pp. 221-226 (1983).

N. Kollias et al., "Erythema and Melanogenesis Action Spectra in Heavily Pigmented Individuals as Compared to Fair/Skinned Caucasians," *Photodermatol Photoimmunol Photomed*, vol. 12, pp. 183-188, (1996).

J.A. Parrish et al., "Erythema and Melanogenesis Action Spectra of Normal Human Skin.," *Photochem. Photobiol.*, vol. 36, pp. 187-191, (1982).

G. Plewig et al. A New Apparatus for the Delivery of High Intensity UVA and UVA+UVB Irradiation, and Some Dermatological Applications, *British Journal of Dermatology*, vol. 98, pp. 15-24, (1978).

Internet Marketing Material, "ReLume™ Revolutionary Technology for Restoration of Lost Pigment," 3 pages in length.

Marketing Material, "Altus CoolGlide® Hair Removal Laser System," 2 pages in length, (2002).

"DC-DC Power Converters, *Wiley Encyclopedia of Electronics Engineering*," J. Webster (Ed.), John Wiley & Sons, Inc., pp. 53-63, (1999).

Final Office Action received for U.S. Appl. No. 11/051,887, mailed on Apr. 19, 2010, 6 pages.

Non Final Office Action received for U.S. Appl. No. 11/051,887, mailed on Oct. 7, 2009, 7 pages.

* cited by examiner

SYSTEM AND METHOD FOR DERMATOLOGICAL LESION TREATMENT USING GAS DISCHARGE LAMP WITH CONTROLLABLE CURRENT DENSITY

PRIORITY

This application claims the benefit of U.S. Provisional No. 60/977,609, filed Oct. 4, 2007.

BACKGROUND

High-intensity light can be applied to skin for various medical treatments. Common sources of electromagnetic radiation used for dermal and epidermal treatments include lasers, flashlamps, and RF sources. In the past, for example, skin has been treated with EMR to provide for hair removal, and other skin treatments.

In part because of the cost associated with laser systems, efforts were made to develop direct filtered flashlamp treatment devices, sometimes referred to as intense pulsed light devices, or IPL devices. These IPL devices are generally less expensive to produce and operate than lasers. The different quality of light from IPL devices (non-monochromatic, incoherent and divergent) is generally acceptable for many epidermal and dermal applications, as opposed to some other applications where lasers have traditionally been used, such as ophthalmology procedures where tight focusing and low divergence of the treatment energy can be crucial.

Dermatological flash lamps and associated systems are described in the following pending applications owned by the assignee of the present application: U.S. application Ser. No. 10/351,981, filed Jan. 7, 2003 (US Publication No. US 2004/0147985), U.S. application Ser. No. 11/051,887, Filed Feb. 4, 2005 (US Publication No. US 2005-0177141), and U.S. application Ser. No. 11/414,441, filed Apr. 28, 2006 (US Publication No. US 2007-0255265). Each of these applications is hereby incorporated herein by reference.

The present application discloses a flashlamp system and various methods for using the flashlamp system. In a disclosed embodiment for treatment of dermatological lesions, current density control is used to tailor the spectral distribution so that it is most suitable for the type of lesions to be treated (e.g. pigment lesions or vascular lesions including facial telangiectasias or diffuse redness). According to one disclosed method, a user identifies a type of facial lesion present in an area of skin to be treated, and selects between a first treatment mode that will operate the flashlamp at a first current density that will produce a first spectral output tailored for a first type of lesion, or a second (or third etc.) treatment mode to operate the same flashlamp at a different current density to operate the flashlamp at a second current density tailored for a different type of lesion. This method can obviate the need for changeable filters or handpieces on a dermatological treatment system.

DETAILED DESCRIPTION

Figure 1:
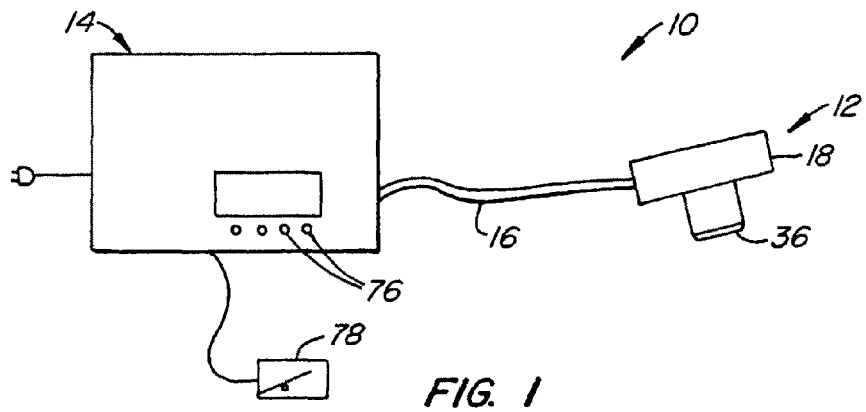
FIG. 1 is a simplified schematic illustration of a dermatological treatment flashlamp assembly.
Figure 2:
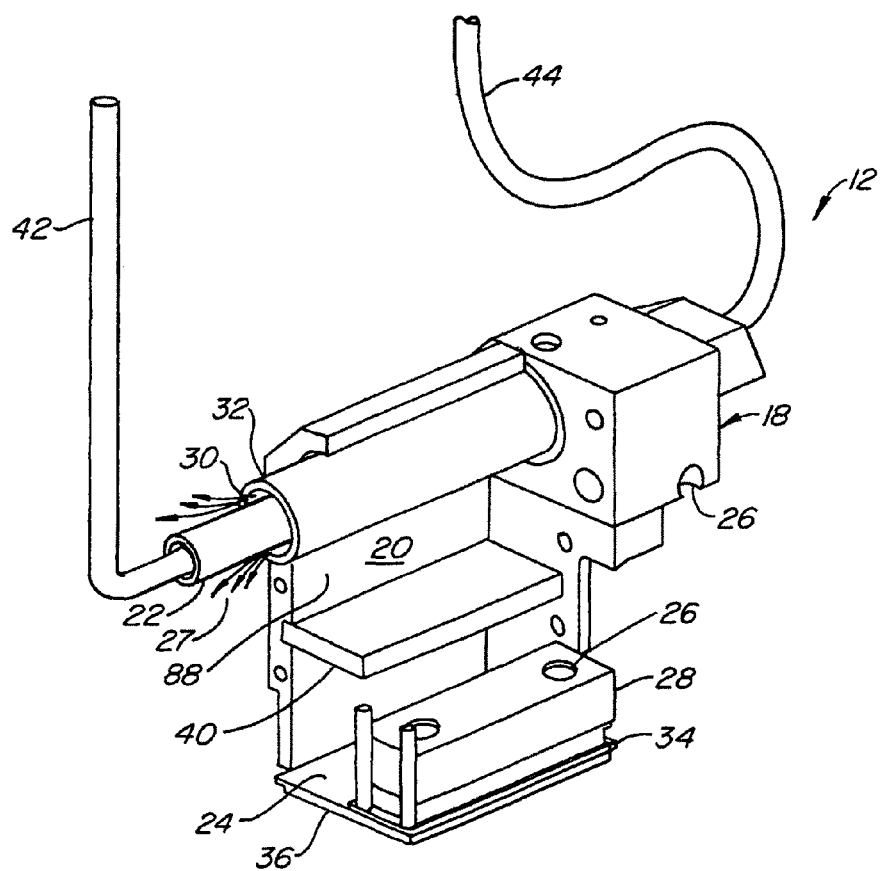
FIG. 2 is an isometric view of the major operational components handpiece of FIG. 1 with portions broken away to show various elements.
Figure 1A:
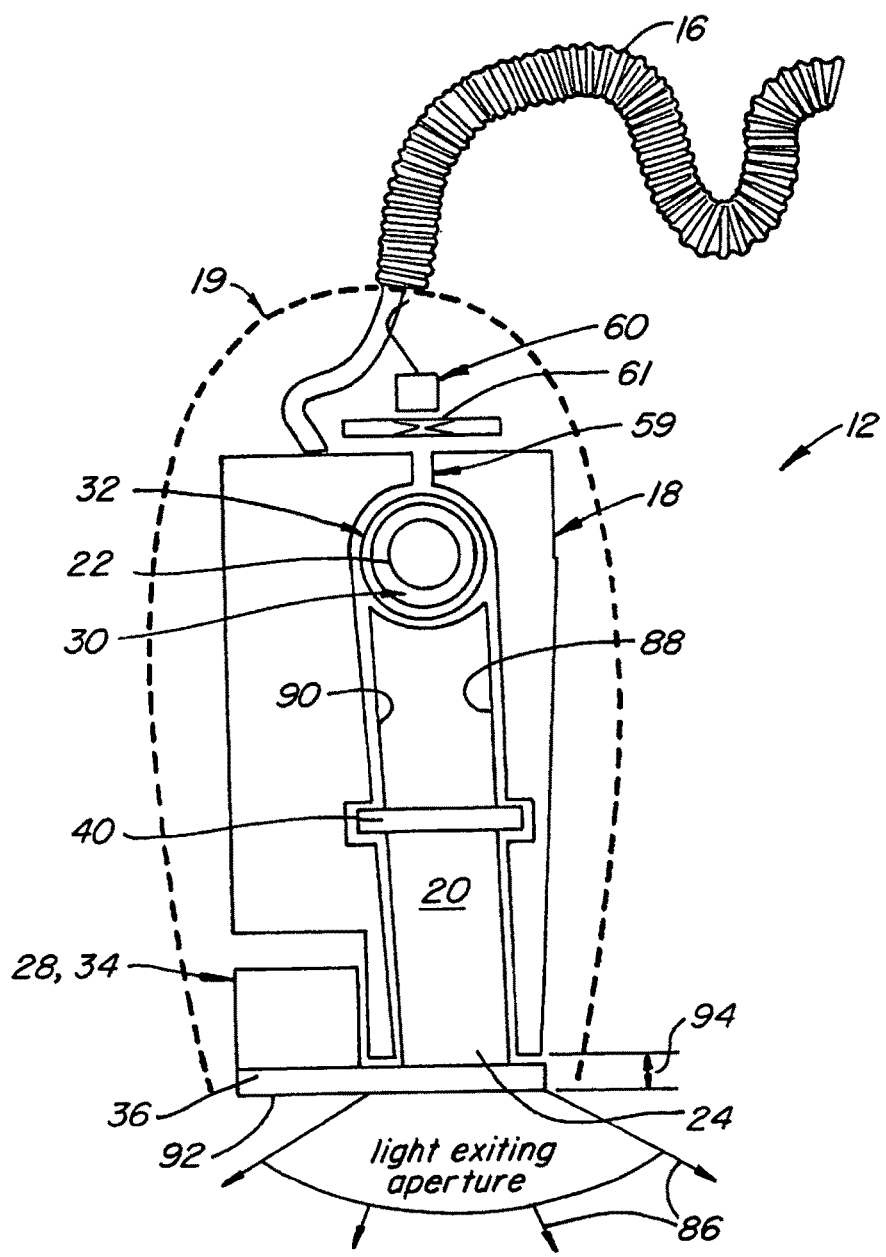
FIG. 1A is a simplified cross-sectional view of the components of the handpiece of FIG. 1.
Figure 3:
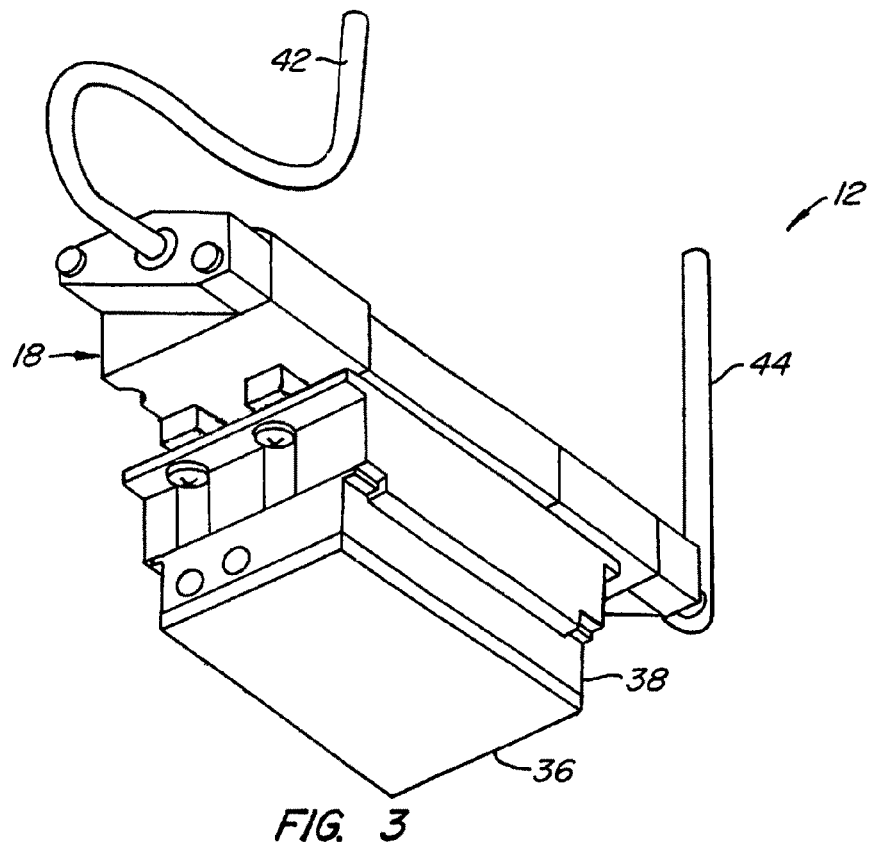
FIG. 3 illustrates the components of FIG. 2 in an assembled condition as viewed from the skin-contacting surface.

FIG. 1 illustrates a dermatological treatment flashlamp assembly 10 including a handpiece 12 connected to a power and control assembly 14 by a conduit 16. Handpiece 12, shown in FIGS. 1A, 2 and 3, comprises a housing 18, typically made of aluminum for its good thermal conductivity and its ability to have highly reflective surfaces, within a shell 19. Housing 18 defines a housing interior 20. Flashlamp 22 is mounted at one end of housing interior 20 with an aperture 24 formed at the opposite end of housing interior 20. Housing 18 defines a number of coolant channels 26 through which a coolant 27, typically distilled water, flows to remove heat from handpiece 12. In particular, coolant 27 passes through a heat sink 28 positioned adjacent to aperture 24 as well as through a gap 30 formed between flashlamp 22 and a UV-absorbing flowtube 32. Heat sink 28 is used to transfer heat away from the hot side of a thermoelectric device 34 sandwiched between a skin-contacting sapphire cover 36 and the heat sink.

Sapphire cover 36 substantially covers the outer end 38 of handpiece 12 and thus covers aperture 24 as well as thermoelectric device 34. The use of sapphire instead of, for example, glass for cover 36 is desirable because sapphire not only permits radiation from flashlamp 22 to pass through aperture 24 and to a patient's skin, but is an excellent heat conductor. This permits thermoelectric device 34 to more effectively cool skin-contacting window 36 helping to prevent patient discomfort and, in some situations, unintended tissue damage. Coolant 27 passes along appropriate tubes, not shown, to and from handpiece 12 along conduit 16; electrical energy is supplied to flashlamp 22 along leads 42, 44 which also pass along conduit 16. Coolant 27 may be recycled using a heat exchange or may be replaced with fresh coolant.

Flowtube 32 blocks the passage of UV radiation, typically of wavelengths below about 350 nm, by absorbing the UV radiation and converting it into heat. The longer wavelength radiation passes into housing interior 20 and through a long wave pass filter 40 situated between flashlamp 22 and aperture 24. Filter 40 may be constructed to simply absorb shorter wavelengths or to reflect shorter wavelengths, or both absorb and reflect shorter wavelengths. It is currently preferred to provide filter 40 with a coating which reflects some shorter wavelengths to reduce the heat buildup within filter 40. This reflected radiation may be absorbed by the walls of housing 18, by flowtube 32 or by flashlamp 22, all of which are cooled by coolant 27. Together, flowtube 32 and filter 40 act as a notch-type light passage restricting mechanism, typically called a notch-type filter.

In one embodiment different filters could be used to achieve different EMR outputs. These different filters could provide for example three wavelength ranges, a long wavelength pass (such as about 580 or 590 or 600 or 610 nm and longer), a wide notch (590-850 nm) and a narrow notch (590-700 nm). In the notch filter embodiments, the heat load to tissue and to cover 36 can be reduced, while still producing the intended tissue effect, by a factor of about 2-10 depending on whether a narrow notch filter is used (with the heat load reduced by a factor of about 4 to 10), or a wide notch filter (with the heat load reduced by factor of about 2 to 5). This can result in the need for less cooling power, which can result in a smaller handpiece and more ergonomic design. Reduced heat load also creates a larger safety margin and can speed up treatment because there may be no need to stop to cool the window, as is often required with conventional devices. The reduced heat load may eliminate or reduce the need for use of a cooling gel.

Generally it may be desired to produce a broad wavelength band of, for example, 500-1100 nm for various dermatological treatments such as hair removal, small vessel or telangiectasia coagulation. However, in the treatment of pigmented lesions, such as solar lentigines, poikiloderma of Civette, melasma, hyperpigmentation, the purpose is to target relatively shallow pigments while avoiding strong absorption by hemoglobin in blood and vascular tissue, in which absorption peaks are located between 500 and 590 nm. Therefore, in such situations it may be desirable to limit the wavelength band to a shallow tissue-penetrating, but still strongly melanin-absorbing wavelength spectrum, such as 590-850 nm or 590-700 nm. Doing so helps to limit the depth of penetration of the radiation, which is quite shallow when treating pigmented lesions, thus reducing unnecessary tissue damage and patient discomfort. While a notch filter approach has several advantages in several situations, obtaining appropriately large flux levels using a notch filter approach creates practical difficulties. Therefore, a long wavelength pass embodiment may be preferred, especially for light skinned individuals or individuals with less melanin concentration in the targeted lesions.

Other filters are discussed below in connection with an alternative embodiment tailored for various types of lesion removal.

Figure 4:
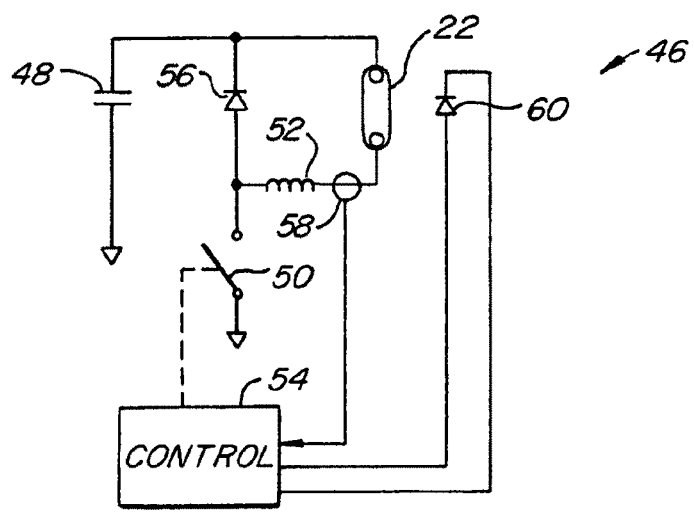
FIG. 4 is a schematic diagram of the basic components of the controlled current source power supply of FIG. 1.
Figure 5:
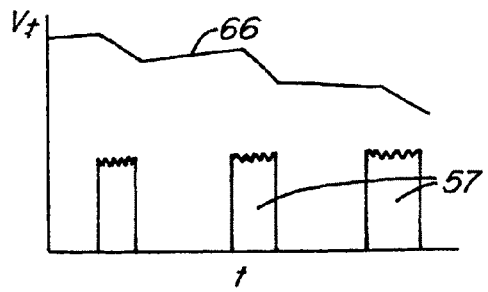
FIG. 5 is a plot of voltage vs. time for the capacitor of FIG. 4 and an associated series of constant voltage/current pulses.

Assembly 14 also includes a power supply 46, shown schematically in FIG. 4. Power supply 46 is a controlled chopper circuit with an inductive filter element, operating in a pulse width modulated controlled current mode (in which the current is controlled and the voltage is not controlled). Power supply 46 may of a type similar to the Xeo platform sold by Cutera, Inc. of Brisbane Calif. and presently used to power dermatological lasers and flashlamp devices, or one similar to the CoolGlide® laser system for hair reduction and vascular indications, also sold by Cutera, Inc. of Brisbane Calif. Alternatively, power supply 46 could be operated in a pulse width modulated controlled voltage mode (in which the voltage is controlled and the current is not controlled) or in a controlled power mode (in which the voltage and/or current are controlled in a manner resulting in controlled power). Energy storage capacitor 48 is charged to a level allowing the desired energy to be delivered without unacceptable lamp voltage droop at the desired current. Switch 50 is closed which ramps up current through lamp 22, inductor 52, and switch 50. When the appropriate current is reached, the control circuit 54 turns off the switch 50 and the current flow diverts to the diode 56. When the current flow decays to an appropriate level (typically 75% of the peak value) the control circuit again turns on the switch 50 and the cycle repeats until a pulse 57 is complete. This turning of switch 50 on and off during a single pulse 57 creates a slight ripple in pulse 57 as indicated in FIG. 5. The operation of assembly 40 in a controlled power mode refers to both the electrical energy delivered to lamp 22 and the resulting controlled optical power from lamp 22. Current sensor 58 and photodiode 60 are used independently or in concert to control the optical power delivered to skin. Photodiode 60, see FIG. 1A, may be placed at the top of housing 18 opposite a pair of apertures 59, and 61. The treatment waveform of the optical energy created by lamp 22 corresponds generally to the treatment waveform of the electrical energy delivered by power supply 46 to lamp 22.

Lamp life is a concern in high-energy flashlamp systems. Instead of using a treatment waveform comprising one large pulse tens of milliseconds long, according to the present invention the power supply can modulate the lamp power in such a manner that the treatment waveform comprises many shorter, slightly higher power pulses with small gaps between them. The gaps decrease the stress and load on the lamp elements, and this reduced loading should result in longer lamp life. For example, instead of supplying a flashlamp with a treatment waveform comprising a single pulse 20 ms long, the flashlamp can be supplied with, for example, a treatment waveform comprising one or more of the following power pulse sequences: 8 power pulses each 2 ms long separated gaps approximately 0.6 ms long; 4 power pulses each 4 ms long separated gaps 0.75 ms long; 16 power pulses each 1 ms long separated gaps 0.25 ms long; 2 power pulses each 9 ms long separated gaps 2 ms long. In addition, a power pulse sequence may include power pulses of different durations separated by the same or different length gaps or of power pulses of equal durations separated by different length gaps.

In the present embodiment, the chopper circuit allows for current controlled operation of flashlamp 22. In current controlled operation, the impedance value of the lamp does not determine the amount of current that the driver can supply to the lamp. This has several consequences: A short flashlamp arc length 62 (or any other length) relative to the aperture length 64, see FIG. 7, can be used, thereby matching the desired treatment type and size, with attendant increase electrical-to-optical efficiency, a reduced stored energy requirement, and a more ergonomic handpiece design through a reduction in the required lamp dimensions. It is presently preferred that flashlamp arc length 62 be about equal to-about 10% longer than, aperture length 64; that is, it is preferred that length 62 be approximately 20 percent longer than the treatment area width (typically 3 cm) in order to reduce end effects associated with the optical performance of the lamp arc in the region of the lamp electrodes. Arbitrary control of the lamp power waveform allows for a wide range of pulse amplitudes and widths. Arbitrary waveform generation is possible using power supply 46 but is not possible with PFN or RDC circuits. The range over which arbitrary lamp currents can be set with power supply 46 is typically 10:1, which can be selected within one pulse. RDC circuits can only set up for one current during a pulse and must accept the voltage and current droop associated with energy depletion of the storage capacitor, or else the size of the capacitor must be very large so as to store a large amount of energy relative to the amount of energy discharged through the lamp during a pulse. Capacitor voltage drops 66, 68, see FIGS. 5 and 6, do not affect output power as in the RDC circuit. This allows constant power pulses 57 to be generated with less stored energy. In a preferred design the capacitor voltage can drop by 50% before output power is affected at all. In a typical RDC design a capacitor voltage drop of 50% results in an 87% reduction in output peak power.

Figure 6:
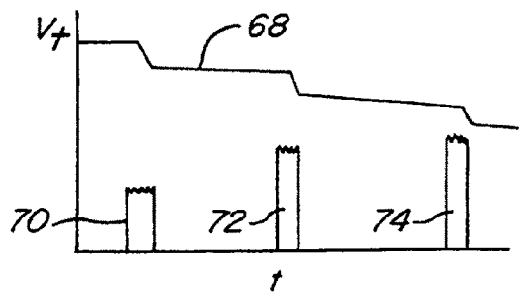
FIG. 6 is a plot similar to that of FIG. 5 in which the pulses have different, in this case increasing, voltage/current amplitudes.
Figure 7:
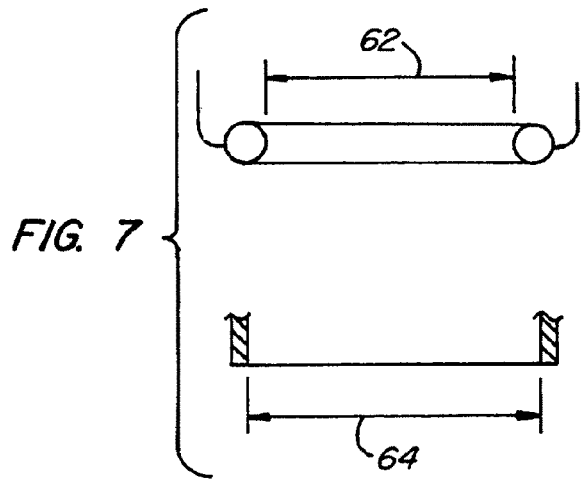
FIG. 7 is a simplified view illustrating the relationship between the flashlamp arc length and the aperture length for the handpiece of FIGS. 2 and 3.

FIG. 6 illustrates a treatment waveform comprising an arbitrary pulse train, consisting of several pulses 70, 72, 74 of selected amplitudes, durations, intervals etc., to achieve the most effective treatment. In this example, successive pulses increase in amplitude in a potentially useful therapeutic treatment. Some pulse widths and constant or near-constant pulse amplitude (light intensity) combinations can be achieved with a controlled current source, such as power supply 46, that the PFN and RDC circuits in the non-notch filter versions either cannot achieve or require an impractical or uneconomical energy storage bank. Specifically, pulse widths >5 ms in combination with fluences in the >10 J/cm2 range are achievable with power supply 46 in the long wave pass (non-notch) embodiment but do not appear to be practical with these other technologies.

Figure 8:
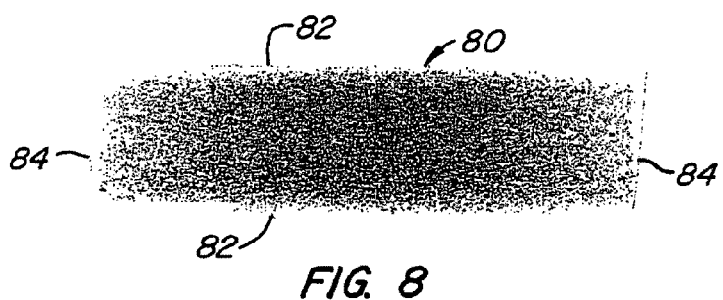
FIG. 8 illustrates a typical flashlamp spot geometry for the handpiece of FIG. 1A.
Figure 9:
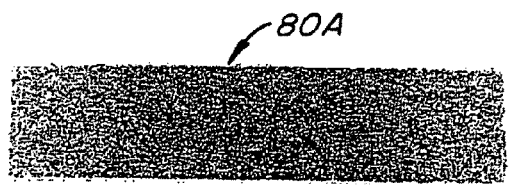
FIG. 9 illustrates a conventional flashlamp spot geometry.

Aperture 24 of handpiece 12 is rectangular and housing interior 20 has a rectangular cross-sectional shape. They could, however, have other shapes as well. Typical flashlamp spot geometry 80 for handpiece 12 is shown in FIG. 8. Flashlamp spot geometry 80 is also generally rectangular with the longer sides 82 and shorter ends 84. The intensity profiles along both sides 82 and ends 84 are not sharp but rather are "feathered" with smoothly decreasing intensity. This is in contrast with conventional flashlamp optical intensity profiles, which typically have sharply delineated edges; one example of a conventional flashlamp spot geometry 80A, often termed a "top hat" geometry, is shown in FIG. 9. The feathered edges along sides 82 and ends 84 are created through a combination of an increase in the divergence of the light passing through aperture 24 and in the stand-off distance produced by the separation between the aperture 24 and the exit surface of the sapphire cover 36. This separation distance 94 is preferably about 1 to 5 mm, and more preferably about 2 to 4 mm. In one embodiment distance 94 is about 2.5 mm. The aperture 24 area, the divergence of the light, and the sapphire cover 36 thickness are chosen to allow for both a reasonably small spot geometry 80 and divergent, and therefore shallowly penetrating, optical intensity profile. Also, feathering of the edges may be useful for placement of treatment spots adjacent to one another without producing sharply contrasting treatment zones, which tend to be cosmetically unacceptable.

Melanin-containing pigmented lesions are in the epidermis or upper dermis so that it is very useful to limit the radiation to a shallow tissue-penetrating (aided by divergence), strongly melanin-absorbing wavelength spectrum. In the embodiment shown in FIGS. 1A and 2, this divergence, illustrated schematically by arrows 86, is enhanced. Reflective surfaces 88, 90 converge relative to another (by tapering downwardly and inwardly along their entire lengths) to enhance the divergence of the radiation along sides 82. Convergence may also be created by, for example, one or more of curving, stepping or tapering of at least a portion of at least one of the reflective surfaces.

Handpiece 12 may be selected according to the particular procedure to be conducted and the width (dimension) of the treatment area. Using controls 76 of assembly 14, the user may input one or more parameters, such as pulse width or widths, the optical fluence for each pulse, the period between pulses (which may be the same or different), the number of pulses delivered each time foot switch 78 is depressed. Power supply 46 of assembly 10 is preferably a chopper circuit with an inductive filter operating as a pulse width modulated current supply, and may also operate as a pulse width modulated supply, that is optically power regulated. The waveform selected may have a generally constant current value equivalent to an optical fluence of at least about 1 J/cm2 (such as for narrow notch filter treatment of superficial lentigines in heavily pigmented skin) or at least about 4 J/cm2 (such as for lighter skin) or at least about 10 J/cm2 (such as for light lentigines in light skin). Also, a specific spectral range may influence the optical fluence so that, for example, the optical fluence for the narrow notch embodiment would typically not go above about 10 J/cm2 and the long wavelength pass embodiment would typically not be used below about 3 J/cm2. The waveform selected may also have a generally constant current value equivalent to an optical peak power producing a total fluence of between about 2 and 50 J/cm2. The waveform selected may have a generally constant current value equivalent to an optical fluence of at least about 10 J/cm2 with a pulse width of at least about 5 ms. The waveform may be selected to have a generally constant current value with a pulse width of about 1 to 300 ms, or about 5 to 50 ms, or about 10 to 30 ms. The waveform selected may have a generally constant current value and may be substantially independent of pulse width or repetition rate. The settings will depend upon various factors including the type of treatment, the size of the lesion, the degree of pigmentation in the target lesion, the skin color or phototype of the patient, the location of the lesion, and the patient's pain threshold. Some or all of the operational parameters may be pre-set and not be user-settable. In one embodiment, the bandwidth spectrum, which could be any range of spectrums such as 560-1100 nm, 590-850 nm, and 590-700 nm, will generally be fixed for a particular handpiece 12. However, it may be possible to construct handpiece 12 so that appropriate wavelength filters and reflectors may be changed by the user to change the wavelength of the output radiation. After the appropriate settings have been made, the flow of coolant 27 is actuated through the use of controls 76. Cover 36 of handpiece 12 is placed at the target site on the patient's skin, foot switch 78 is depressed, causing radiation to pass from flashlamp 22 through cover 36 at aperture 24, and the user begins moving handpiece 12 over the patient's skin. The thermoelectric device 34, and to a lesser extent coolant 27 operate to keep the sapphire cover 36 from overheating during use while the radiation treats the pigmented lesion.

Another embodiment is directed to producing cosmetically desirable pigmentation in the skin in a spatially and temporally controlled manner. Melanin synthesis in melanocytes, or "melanogenesis", refers to this process. Melanogenesis can take place as a photoprotective effect in response to UV radiation, and when it occurs in response to natural or artificial UV light, it is referred to as "tanning."

A distinct phenomenon associated with true melanogenesis also occurs upon exposure to UV and visible light. "Immediate pigment darkening" (IPD) is a transient oxidative change to the state of existing melanin, occurs mostly in darker skin phototypes. The persistence of IPD is hours to days, and is not clinically useful in itself for treating pigmentation cosmetic problems. Strong IPD in dark skin phototypes indicates that longer-term (days to onset) melanogenesis will take place, and may serve as a clinical endpoint to pigmentation phototherapy [see Kollias N, Mallallay Y H, Al-Ajmi H, Baqer A, Johnson B E, Gonzales S. "Erythema and melanogenesis action spectra in heavily pigmented individuals as compared to fair-skinned Caucasians", Photodernatol Photoimmunol Photomed 1996: 12: 183-188].

According to published melanogenesis action spectra [see Parrish J A, Jaenicke K F and Anderson R R. "Erythema and melanogenesis action spectra of normal human skin", Photochem. Photobiol. Vol. 36. pp. 187-191, 1982], there is a strong dependence on wavelength, with the threshold dose rising rapidly as the wavelength increases from the end of the UVB (280-320 nm) into the UVA (320-400 nm). Beyond 400 nm, there is very little melanogenesis. The minimum melanogenic dose (MMD) to achieve/obtain threshold pigment induction is on the order of 100 J/cm2 for 365 nm, 1-10 J/cm2 for 315 nm, and 0.1 J/cm2 around 300 nm. The MMD is roughly independent of skin phototype. [Parrish, et al., 1982.]

One embodiment of flashlamp 22 can provide delivery to skin of a maximum pulse of light of fluence 30 J/cm2 (in a 20 ms pulse) in the 350-1100 band. That means that approximately 3 J/cm2 (in 20 ms) is available in the UVA and about 1.5 J/cm2 (in 20 ms) in the UVB. Since the minimum melanogenic dose (MMD) for UVB is falls between 0.1 and 1.0 J/cm2, a few pulses of appropriately filtered light from handpiece 12 would induce intermediate-term persistence melanogenesis (tanning) over the course of a few days post-treatment. In particular, a filter or filter set substituted for the epidermal pigment removal filter 40, having a transmission band between 290 and 320 nm could deliver to skin between 0.1 and 1.0 J/cm2 in a single 20 ms flash. One or more flashes could be directed to specific local areas of the skin at which increased pigmentation is desired. Masking agents, such as sunscreens or other physical barriers could be interposed between the light aperture and the skin to produce specific shapes or small areas of exposure (smaller than aperture 24 of handpiece 12).

Similarly, one could use UVA light by selecting another filter or filter set that allows light between 320 and 400 nm to be transmitted and delivered to the skin. The available fluences in this band are somewhat higher than in the UVB. s above, as much as 3 J/cm2 (in a 20 ms flash pulse) could be delivered with the preferred flashlamp 22. In this case, since the MMD is so much higher (as much as 100 J/cm2) many pulses would have to be delivered, potentially numbering into the hundreds of pulses. However, since these pulses could be produced by power supply 46 at as much as 0.5 Hz in this example, a particular treatment area could be exposed to the desired amount of UVA in as little as (100 shots)*(0.5 Hz)=200 seconds.

In the case of UVA treatments, the pulses would typically be delivered at a modest repetition rate to prevent any thermal effects or heat buildup. For UVA highest average power treatments, the average power loading would be approximately (3 J/cm2)(0.5 Hz)=1.5 W/cm2. Some conduction cooling of the sapphire window, and possibly the skin would likely be needed in this case. Sapphire cover 36 in combination with the existing temperature stabilizing thermoelectric device 34 can, for example, remove at least 10 W average power from the skin plus cover 36. Other wavelength spectra, including continuous and discontinuous spectra over one or both of the UVA-UVB spectrum, may be desirable.

Several advantages exist when the system is adapted for providing pigmentation of the skin, including (1) easy control of treatment areas, placement and doses, (2) ability to adapt a particular wavelength filtering handpiece to a particular treatment (3) confinement of UV exposure to superficial layers of the epidermis and dermis through the beam divergence (through the reflector geometry) (4) "feathering" of the light intensity pattern by a combination of divergence control and optical window standoff distance between the reflector aperture and the skin.

Control of Spectral Properties

Much of the discussion below is directed to new embodiments utilizing a flashlamp, and the controllable power supply to provide for control of the spectral properties of electromagnetic radiation output by the flashlamp.

It should also be noted that much of the discussion herein refers to a flashlamp as being the source which generates the light (or more broadly speaking electromagnetic radiation EMR) which is used to treat the skin; however, a flashlamp is part of a more general category of gas discharge lamps, which could for example include different arc lamps, and any gas discharge lamp (GDL) capable of the generating pulses of relatively intense energy in a relatively short amount of time could be used in an embodiment of the system and method herein; thus, the term flashlamp as used herein should be interpreted as including any GDL capable of such performance.

Figure 10:
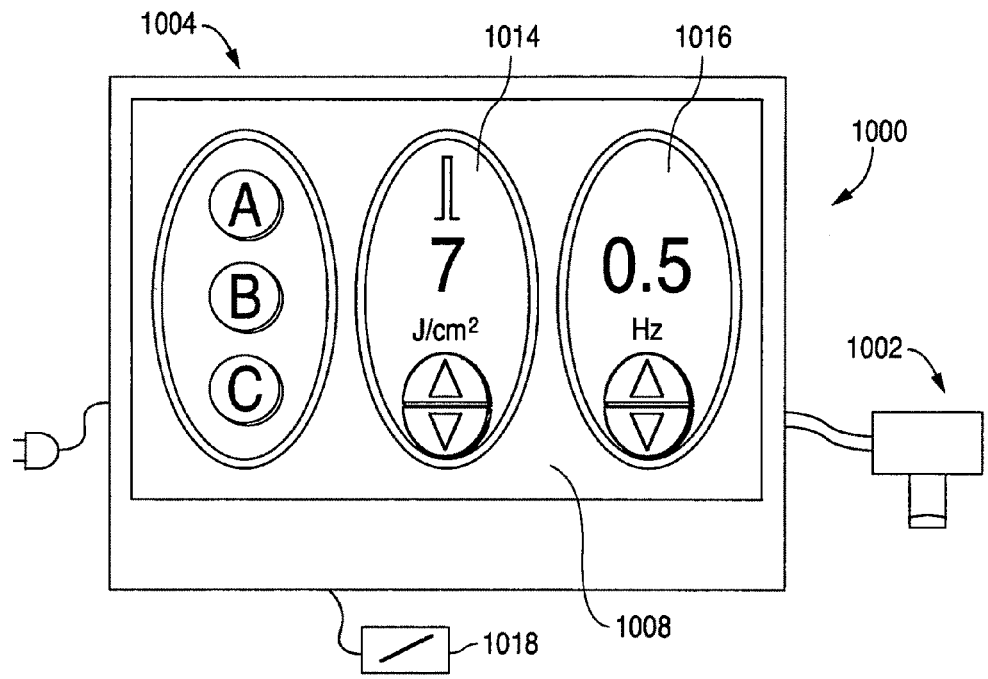
FIG. 10 illustrates an embodiment of system herein, which provides for spectral control.

FIG. 10 shows an embodiment of a dermatological treatment flashlamp assembly 1000 including a handpiece 1002 connected to a power and control assembly 1004 by a conduit 1006. The assembly 1000 can include a power supply as described in more detail below. The element 1008 of assembly 1000 corresponds to a user interface where a user can input different parameters which will control the operation of the power supply. In the embodiment of FIG. 10, the element 1000 is a touch screen display which can be programmed to provide for a range of different user interfaces depending on the type of handpiece 1002 connected to the system. In the embodiment of FIG. 10, the handpiece 1002 contains a flashlamp, and a filter which are designed to provide for hair removal treatments. In the user interface 1008, a user can select between different display buttons shown as A, B and C. Each of these different buttons provide for controlling the power supply to drive the flashlamp to output EMR having different spectral distribution. As discussed below it is advantageous to be able to provide EMR having a different spectral distribution to provide different hair removal treatments to different skin and hair types.

It is noted that other types of handpieces could be used for providing different types of treatments and in response to a different handpiece being connected via the conduit 1006, a processor in the assembly 1004 would generate a different user interface 1008 on the touch screen display. Aspects of a flexible modular assembly for driving and providing a user interface for different handpieces are described in detail in the U.S. patent application Ser. No. 10/788,821, and Provisional Application Nos. 60/540,981 and 60/532,016 which are incorporated herein by reference.

The handpiece 1002 of FIG. 10 is very similar the handpiece described above in connection with FIGS. 1-3, and thus a detailed discussion of all the elements of the handpiece will not be repeated in connection with the handpiece 1002. However, the filter (which would correspond to filter 40 discussed above) of the handpiece 1002, provides for a different range of filtering, than that discussed in the above embodiments. In order to output EMR which is well suited for hair removal treatments, in connection with the system 1000, the filter 40 operates to pass wavelengths longer than about 770 nm, and to block wavelengths below about 770 nm. It is currently preferred to provide filter 40 with a coating which reflects some shorter wavelengths to reduce the heat buildup within filter 40. It should be noted that the cutoff for the long pass filter need not be at 770 nm, and can be changed so that the cutoff wavelength is substantially lower or higher, but generally 770 nm should be a fairly effective cutoff point, so that a wide range of different skin color types could be treated for hair removal using a single handpiece, with current density control has described herein.

In systems using EMR to treat a variety of different skin type for providing hair removal, it is widely understood that darker skin types are more challenging to treat with shorter wavelengths because of the higher absorption of melanin in epidermal tissue. The article *Theoretical Consideration in Laser Hair Removal*, (Dermatologic Clinics, Volume 17, Number 2, April 1999), by E. Victor Ross, et al. which is incorporated herein by reference, describes the ratio between hair bulb temperature (Th) and epidermis temperature (Te) as a function of wavelength for lighter and darker skin.

While in general it is clear that the greater the ratio of Th/Te the better (in terms of hair removal treatments) practical considerations taken into account in embodiments of the system and method describe herein generally provide for minimum ratio of for Th/Te is about in the range of about 1.5 for effective hair removal treatment. Using the 1.5 ratio as a general guideline, methods and systems are able to provide for increasing the temperature of the hair bulb to a sufficiently high temperature to damage the hair bulb, while the surrounding epidermal tissue is maintained at a lower safe temperature. As a practical matter, however, it should be recognized that with sufficient cooling of the tissue being treated the ratio could be significantly below 1.5.

Using the 1.5 ratio as a guideline provides that when an area of skin is treated with therapeutic EMR it should raise the temperature of the tissue being treated such the temperature of the hair bulb is significantly higher than the surrounding epidermal tissue. The temperature of the hair bulb and surrounding epidermal tissue is largely effected by the characteristic of the hair bulb and the surrounding epidermal tissue. For example, it has been found that for light skin, wavelengths as short as about 740 nm, can be used to achieve the desired treatment temperatures and ratio of Th/Te, while for darker skin, where the epidermal tissue of the skin tends to absorb more energy, than lighter skin, wavelengths as short as 825 nm are effective.

The amount of energy needed to elevate Th to temperatures high enough to kill or damage the follicle is a function of the melanin concentration of the bulb and the wavelength of the light. Lighter or finer hairs have less melanin and so at any one wavelength require greater radiant energy exposure than coarse dark hairs. Thus, for example, therapeutic EMR with a wavelength of 900 nm requires 1.5-2 times more radiant energy to elevate Th in a light hair vs. dark hair to the same temperature. Light hair treated with 750 nm light requires approximately the same energy as a dark hair treated with 900 nm. These general principles regarding the heating of hair bulbs are widely known. See, e.g., Ross et al. Also, it should be understood that the discussion of this paragraph assumes that the radiant energy exposure occurs on a time scale which is appropriate for dermatologic treatment and temperature elevations. Generally, this will be somewhere in the range of a few milliseconds, to something less the a 100 milliseconds for treatments using flashlamp—however the time period could very depending on the power of the radiant energy.

An embodiment herein provides a hair removal system which is a relatively efficient device which does not use an excessive amount electrical energy, minimizes the amount of heat generated by the system, and provides for a relatively long lamp life. To achieve this the spectral output of the flashlamp is controlled, to reduce the amount of energy which is generated at wavelengths which provide for less efficient therapeutic treatments for a specific type of skin being treated. Another advantage of using an EMR source which has a controllable spectral make-up for a particular type of skin being treated, is that it allows for lower fluence to be applied to the tissue being treated. Thus, the increased pain associated with higher fluence levels at longer wavelengths, caused in part by the associated absorption by underlying blood vessels, can be reduced. These considerations make it advantageous to minimize energy levels required, using more energy at shorter wavelengths for fair skin and lighter hairs.

An embodiment herein takes advantage of the fact that flashlamps, as well as other gas discharge lamps, generate EMR which has a spectral make-up which is in part a function of the current density being transmitted through the lamp. This approach can offer significant advantages over prior systems which utilized different filters to provide for different spectral outputs. One advantage is that a user need not switch filters to provide treatments to different patients, or to different areas of tissue. Another aspect is that in some cases there tends to be more efficient use of the EMR produced by the lamp, and thus less excess heat is generated, and less wear is incurred by the lamp.

An embodiment herein allows treatment of both lighter and darker skin types, maintaining safe Th/Te ratios with a single device through microprocessor controlled programmable modes. This allows safe, efficacious treatments with an efficient, easy to use device.

Figure 11:
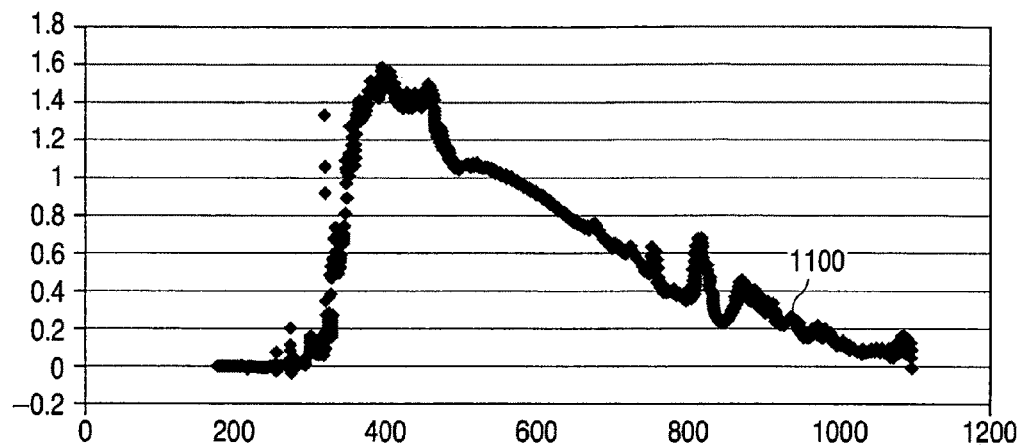
FIG. 11 illustrates spectral output from a flashlamp when driven at a first current density level.
Figure 12:
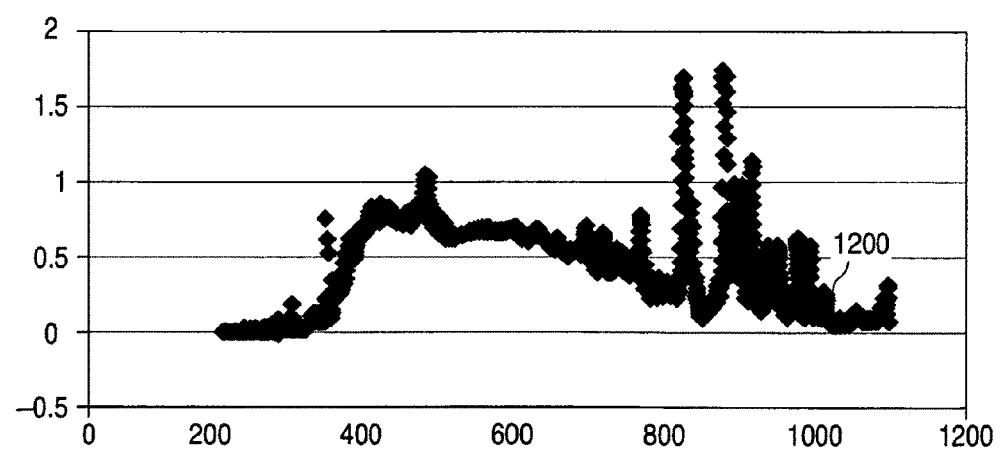
FIG. 12 illustrates spectral output from a flashlamp when driven at a second current density level.

Gas discharge lamps (GDL) in general have the characteristic of an output spectrum dominated by the emission lines of the fill gas at low current densities, with blue-shifted black body emission dominating at high current densities. This well-known effect is illustrated in FIGS. 11 and 12, where FIG. 11 shows the output spectrum 1100 of a xenon flashlamp that is driven at 1824 Amps/cm^2 current density, and FIG. 12 shows the output spectrum 1200 for same lamp driven at 276 A/cm^2.

Figure 13:
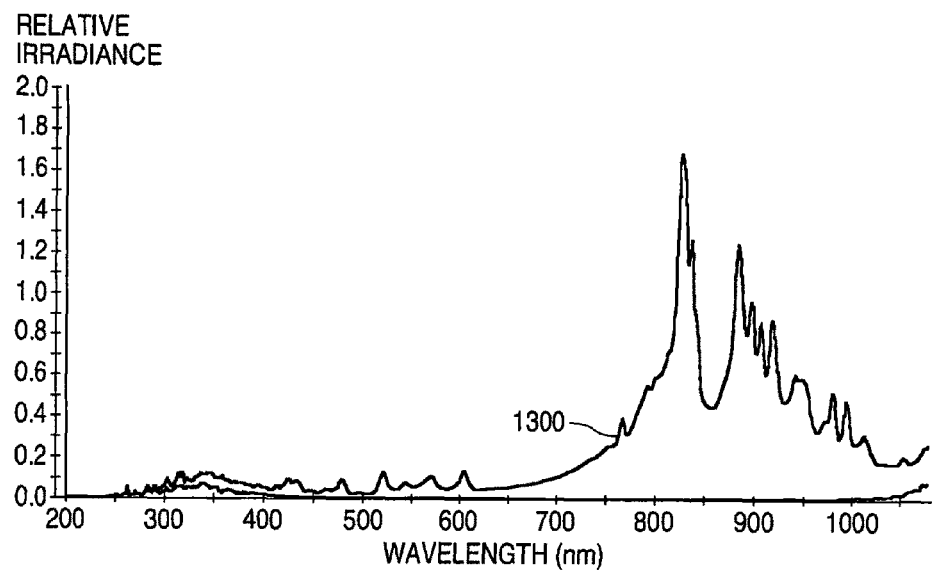
FIG. 13 shows the spectral output from a handpiece of an embodiment herein when driven at a first selected current level and the handpiece has a long pass filter.

The output of the dermatologic system can be varied and controlled to account for one or more characteristics of the tissue where the hair removal treatment is to be applied, by varying the current density to change the spectral distribution output of the flashlamp. For example, referring back to the system 1000 of FIG. 10, where treatment is desired for very lightly pigmented skin, a user can select button A on the user interface. This button could, in one embodiment, correspond to light color skin, for example Fitzpatrick skin phototypes I-III. In response to the selection, the power supply of the system would apply drive current through the flashlamp which corresponds to a desired spectral output. For one particular flashlamp, this could correspond to a current density of 1381 Amps/cm2, but this particular value would vary depending on a particular GDL design. FIG. 13 shows the output spectrum 1300 of a xenon flashlamp in one embodiment of a system herein where the handpiece has a 770 nm filter, and the lamp is driven at 1381 Amps/cm^2 current density.

Figure 14:
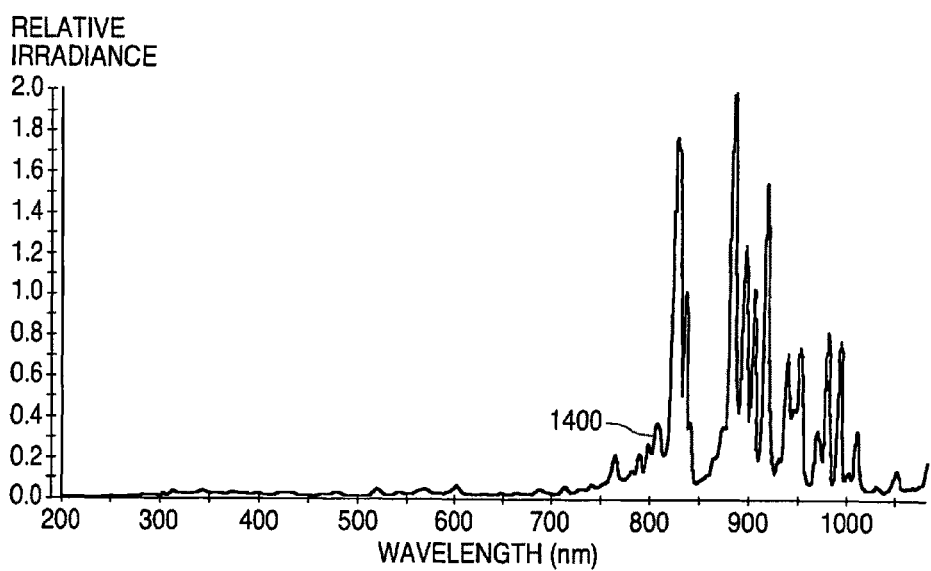
FIG. 14 shows the spectral output from a handpiece of an embodiment herein when driven at a second selected current level and the handpiece has a long pass filter.

When the hair removal treatment is applied to darker areas, for example Fitzpatrick phototypeVI skin, the user could press the button C on the user interface 1008, and the power supply would then drive the flaslamp with a much lower current density. This lower current density would then cause the GDL, in one embodiment a xenon flashlamp, to output therapeutic EMR having a greater component of the output energy at longer wavelengths. For example, in one embodiment using a xenon flashlamp where the user selects the button C, the lamp is driven with a current density of 442 A/cm^2. The spectral output 1400 is shown in FIG. 14. The therapeutic EMR outputs 1300 and 1400 are noticeably different with the high current density output (select A) showing black radiation body dominating relative to the xenon emission bands, which are more prominent in the lower current density output (selection C).

For skin having pigmentation between a lighter range and darker range, the B button on the interface 1008 will provide for an intermediate current density being applied to the flashlamp, and corresponding the spectral output of the lamp, will be somewhere between the spectral outputs provide when buttons A or C are selected.

Figure 15:
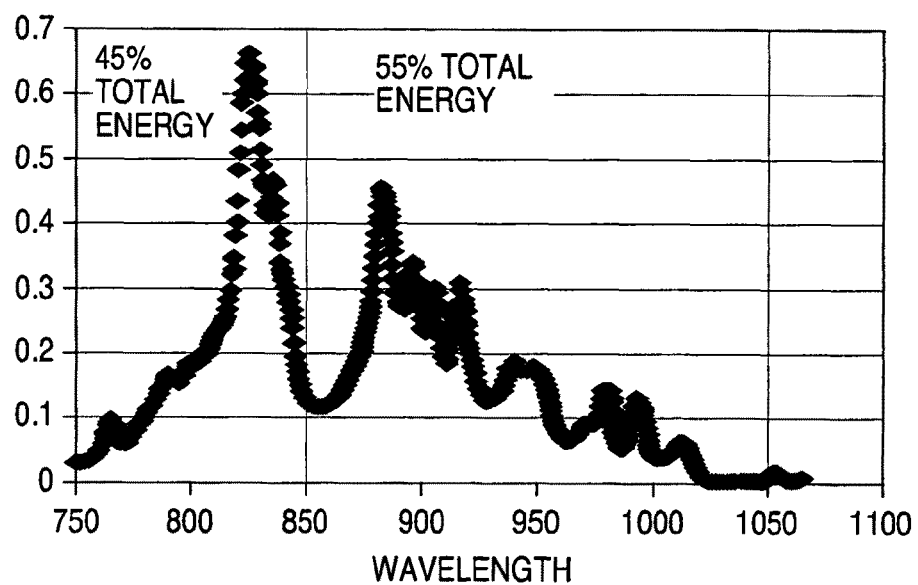
FIG. 15 shows spectral energy distribution corresponding to the spectral output shown in FIG. 13.
Figure 16:
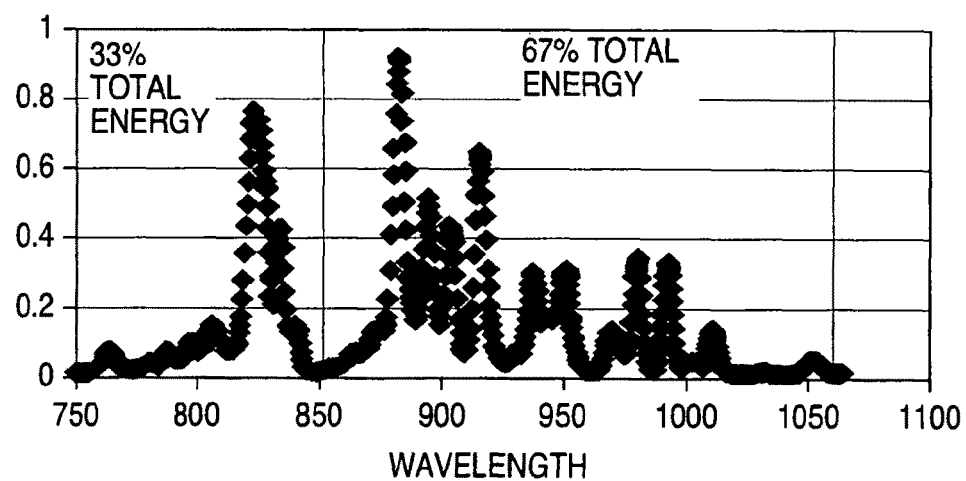
FIG. 16 shows spectral energy distribution corresponding to the spectral output shown in FIG. 14.

FIG. 15 shows information derived from the output spectra 1300 show in FIG. 13; and FIG. 16 shows information derived from the output spectra 14 shown in FIG. 14. FIGS. 15 and 16 show energy for the spectral band 750 nm to 850 nm, and the spectral band 850 nm to 1064 nm bands as a percentage of the total 750 to 1064 spectral energy. In FIG. 15 which corresponds to the therapeutic EMR output when the lamp is driven at setting A, 45% of the energy in the spectral range below 850 nm. In FIG. 16, when the lamp is driven with a much lower current density in correspondence with the setting C, only 33% of the energy is below 850 nm. Thus, by varying the current density, the energy within the 750-850 nm band goes from 33% to 45% with increasing lamp current density from 442 to 1381 A/cm^2. There is a corresponding decrease of 67% to 55% in the 850 nm to 1064 nm band.

Figure 17:
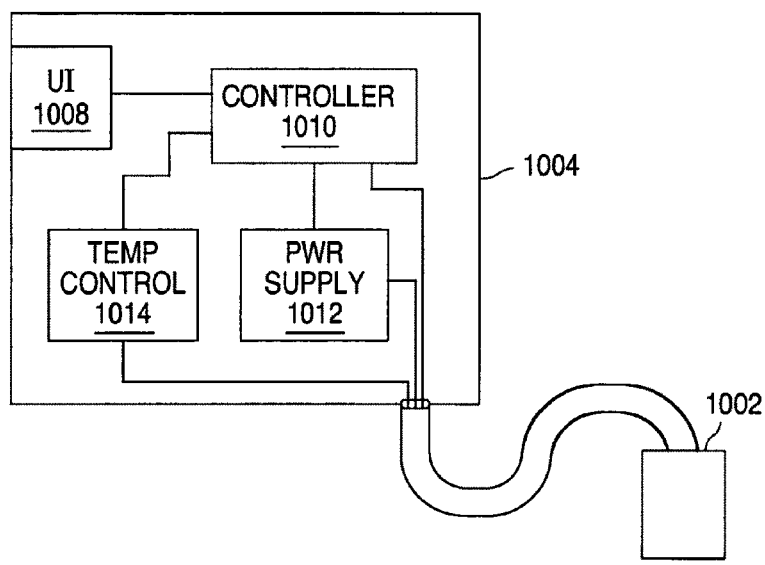
FIG. 17 shows an embodiment of a system herein.

FIG. 17 illustrates additional elements of system 1000 shown in FIG. 10, and shows the relationship between the elements. The user interface 1008 can be a touch screen panel or other user interface device such as bush buttons, dials, or a joystick or in some embodiments a keyboard and a mouse. Input from the user interface is input to the controller 1010. The controller is shown as a single element but could be implemented as a number of processing element distributed through out the system. The controller is communicatively coupled with other elements of the system, including 1002 and can sense the properties of the handpiece. The controller 1010 is also coupled with the power supply 1012 and the temperature control module 1014. In one embodiment the controller can cause the sapphire window to clamp the temperature of the skin in contact with the sapphire window at a selected temperature. Further, in one embodiment the user interface could allow a user to select a temperature to clamp the sapphire window to, and/or the temperature for the sapphire window could be determined based on the A, B or C selection made by the user, where A, B, and C correspond to one or more characteristic of the skin being treated.

Also along the lines of the discussion above, the user interface can allow the user to make selections based on characteristics of the tissue to which the hair removal treatment is to be applied. In response to such a selection by the user of the system the controller will control the power supply to apply a controlled current density to the GDL of the handpiece 1002.

Figure 18:
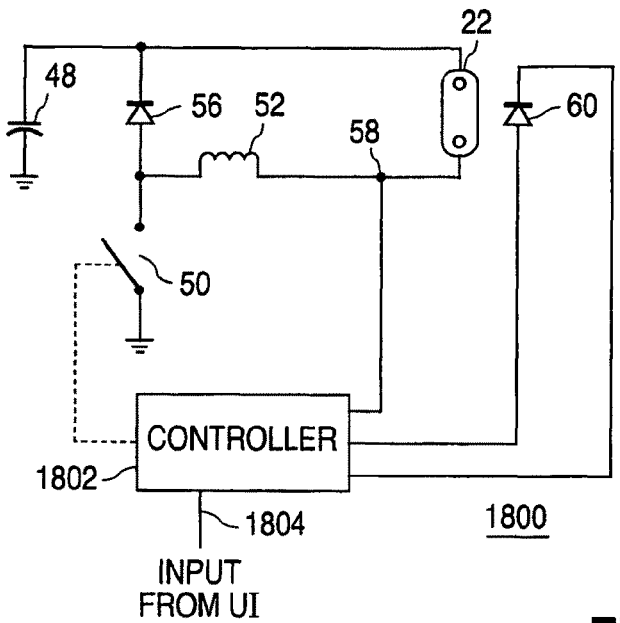
FIG. 18 shows an embodiment of a power supply which controls current density based on user input.

FIG. 18 shows a power supply 1800 which is very similar to the power supply shown in FIG. 4, and accordingly similar number of the elements has been provided, and a detailed discussion regarding all of these elements is not repeated. However, an additional signal 1804 based on the user selection based on the skin phototype and/or hair type to be treated is input to the controller 1802, and the switch is operated to provide for relatively wide range of current densities to the lamp. For example in one embodiment where a user inputs C on the user interface, which corresponds to information indicating that the area of skin being treated is dark skin for example Fitzpatrick phototype VI skin, the controller may refer to a look-up table, or be otherwise programmed to drive the switch of the power supply to output a lower current from the power supply to the lamp, and thus a lower current density through the lamp, than in a situation where a user inputs A on the user interface, indicating a lighter skin color, for Example Fitzpatrick type I skin.

In the system 1000 as shown in FIG. 10, the implementation of the user interface includes a display area which allows a user to select a fluence level for the therapeutic EMR pulse applied to an area of skin. As shown a user selection of 7 J/cm2 has been selected, and this fluence could be increased, or decreased by pressing on the up and down arrows in the area 1014. In the embodiment of system 1016 and area is provided in the display which allows a user to select a pulse repetition rate. For example, as shown a pulse repetition rate of 0.5 Hz has been selected, and this could be increased or decreased. An activation switch 1018 is provided, which could be implemented as a foot switch, wherein the system is activated by stepping on the foot switch.

It should be recognized that different embodiments of a system herein could be adapted to accept a wide range of different user input parameters. For example, one embodiment would allow a user to select a temperature to which the sapphire window of the handpiece will be clamped. One advantage of allowing a user to control the temperature of the sapphire window, is that a user could choose to increase or decrease the temperature of the window, depending a patient's level of pain tolerance.

Additionally, in another embodiment, the user will be able to input a selected pulse width for the therapeutic EMR being applied to an area of tissue being treated. The flexible and highly controllable operation of the power supply of an embodiment of the present system, allows for a system where independent control and variation of pulse width, the amount of fluence, and the spectral output (by controlling the current density through the lamp) can be provided.

Figure 19:
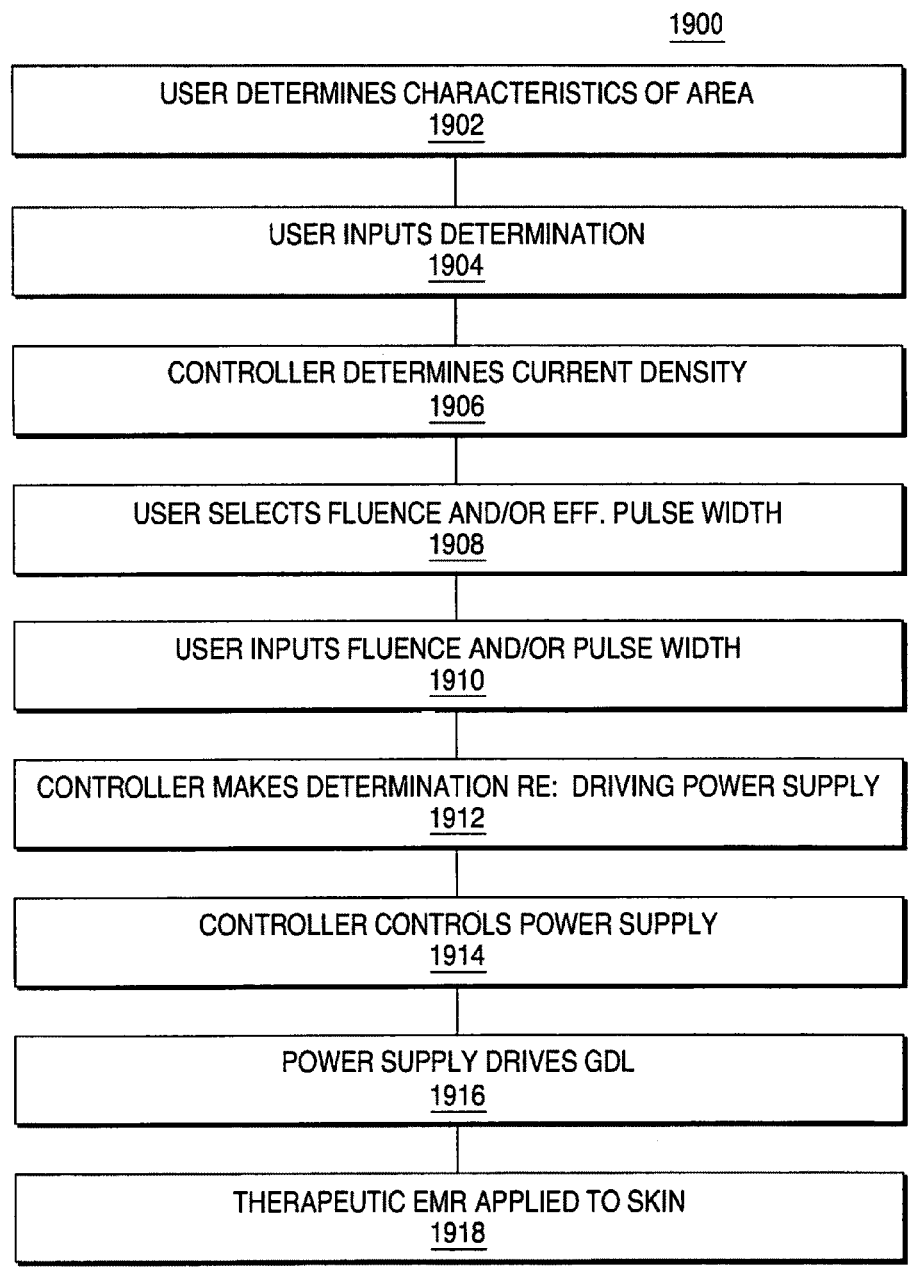
FIG. 19 shows a method of an embodiment herein.

FIG. 19 shows an embodiment of a method 1900 herein. Initially, a user will observe an area of skin where a hair removal treatment is to be applied. The user will make a determination 1902 regarding a characteristic of the skin to be treated. This determination is based on how light or dark the area of skin is to be treated, and/or could also be based on the thickness, and/or color of the hair to be treated. Based on the user's determination regarding the area to be treated, the user inputs 1904 a selection through the user interface of the system (this could for example correspond to the A, B, and C selections shown in FIG. 10). Based on the user input the controller makes a determination 1906 regarding the current density which should be transmitted through the flashlamp, and this current density will correspond to a desired spectral output by the flashlamp. In one embodiment in addition to inputting 1904 a determination regarding the area of skin to be treated, the user can also select 1908 and input 1910 an amount of fluence to be provided to area of skin being treated. Additionally, a user could also be provided with the ability to select an effective pulse width of the therapeutic EMR to be applied to the area of tissue. Based on the user input selections, the controller makes a determination 1912 as to time durations for incremental pulses, and time durations for intervals between incremental pulses, to produce a desired fluence. Based on the user inputs, and the subsequent determinations made by the controller, the controller controls 1914 the power supply to drive 1916 the flashlamp, and the resulting therapeutic EMR output is applied 1918 to the area of skin to be treated.

Figure 20A:
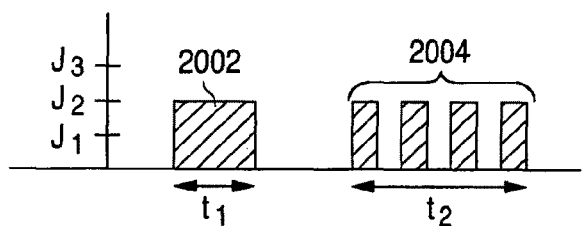
FIGS. 20A-20C illustrate the aspects of the ability to provide independent control over current density, pulse width and fluence.
Figure 20B:
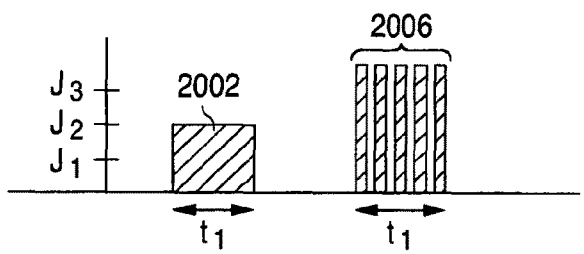

FIGS. 20A-B illustrate some aspects of the operation of the controllable power supply of an embodiment herein, and further illustrates some aspects of the ability to have control over the fluence, current density and pulse width, and the inter-relationship between this parameters, where the vertical axis is current density "J" and the area under the curves relate to fluence FIG. 20A shows first pulse 2002 of current having a duration of t1 which could be used to drive a flaslamp, and would produce corresponding EMR output. Pulses of current 2004 applied over a time duration t2 would apply the same current density the flashlamp of and hence produce the same spectral output from the flashlamp, and the overall fluence of the output EMR would be the same as for pulse 2002. However, the four incremental pulses 2004 with the time interval between the pulses, creates a different effective pulse width in terms of the effect of the output EMR applied to the area of skin being treated. More discussion regarding meaning of effective pulse width is provided below in connection with the discussion of FIG. 20B.

FIG. 20B again shows the pulse 2002, but compares it with a series of incremental pulses 2006, which are applied over a time period of t1. The effective pulse width of the 2002 and the series of incremental pulses 2006 is the same in terms of an output EMR being applied to the skin. Regarding effective pulse width, this is a reference to the fact that where the thermal relaxation time period of the tissue being treated is relatively long, relatively short time intervals between the incremental pulses will not allow time for the any significant decrease in the temperature of the tissue being treated. Generally, the operation in context of the effective pulse width discussion assumes that the peak power in an incremental pulse is sufficiently low as to be below threshold values for ablation of the tissue, or other non-linear effects such as optical breakdown. Thus, during the period when the series of pulses 2006 are being applied to the tissue, the temperature effect is largely as though one pulse of EMR having a duration of t1 were applied to the tissue. While the effective pulse width is the same, the current density for the incremental pulses 2006 is higher than for the pulse 2002, which means there is a different spectral output for the flashlamp and the resulting therapeutic EMR applied to the skin. Further, by adjusting the time interval between each of the current densities the overall fluence of the output therapeutic EMR can be the same for the both the pulse 2002 and the series of pulses 2006.

Figure 20C:
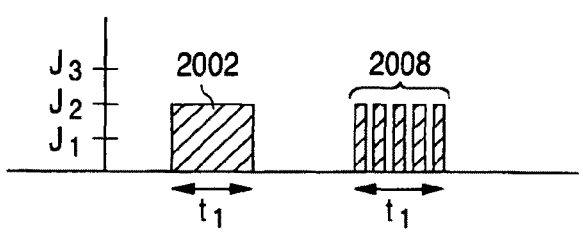

FIG. 20C again shows the pulse 2002, and compares it with a series of pulses 2008. The series of pulses 2008 provide the same current density to the flashlamp as the pulse 2002, so the spectral characteristics of the output EMR will be the same. However, the spacing for between the incremental pulses 2008, the overall fluence of the output EMR is less, although the effective pulse width is the same. FIGS. 20A-C illustrate that for an embodiment herein, independent user selection of appropriate spectral output, fluence and effective pulse width is provided.

Some general aspects of the different elements and operations of different embodiments of systems and methods herein are provided herein. Generally, as is shown by the discussion and figures referred to above, the flashlamp hair removal system uses wavelengths in the infrared range, and reduces or eliminates shorter wavelengths which are more strongly absorbed by melanin. For lighter skin more energy at shorter wavelengths can be utilized than in darker skin, as the lighter skin has less melanin. In general where a higher percentage of shorter wavelength energy is utilized in lighter skin and finer hair, pulse width should be equal to or shorter than the thermal relaxation time of the hair bulb (generally no longer than about 45 to 50 ms). For darker skin with higher concentrations of melanin in the epidermis and hair bulb, the spectral composition of the EMR treatment is more heavily weight to longer wavelengths, and the pulse widths should be longer. Both characteristics allow for epidermal thermal protection while providing for selectivity between the epidermis and the hair bulb.

In one embodiment where a user inputs A, corresponding to lighter skin, the pulse width can be in the range of 4 to 40 ms, depending of the fluence level selected by the user (which in one embodiment is the in the range of 5-50 J/cm2 for light skin); where the user inputs B corresponding to a mid-level skin color, the pulse can be in the range of 20 to 80 ms seconds depending on the selected fluence level; and where input C is selected the pulse width can be in the range of 34 to 102 ms. This range of pulse widths generally provide that for input A the pulse width will be on the same order as the thermal relaxation time of a hair bulb; while settings B and C both have minimum pulse widths significantly longer than the nominal 10 ms TRT of the epidermis.

In one embodiment herein a method and device for EMR treatment of skin and hair removal, is provided which utilizes a xenon flashlamp that has current density control to adjust the spectral output of the lamp to best suit the skin type and/or hair characteristics of the patient to increase both safety and efficacy of the treatment. Stated more generally, an aspect of the invention herein generally relates to methods and apparatus for skin treatments, such as hair removal, using light from gas discharge lamps. More specifically, a treatment is provided with light that has a controllable spectral distribution generated with a current density controlled gas discharge lamp. The spectral distribution chosen is determined by the optical characteristics of the treatment area.

Treatment of Vascular and Pigmented Lesions

A system similar to that shown in FIG. 10 may be used in treatment of pigmented and vascular lesions including facial telangiectasias and cherry hemangiomas, solar lentigines, poikiloderma of Civette, melasma, hyperpigmentation. Treatment (i.e. removal or reduction in appearance) of a target lesion type is achieved by running the lamp at a current density that will produce a spectral distribution appropriate for the type of lesion and/or the amount of pigmentation in the patient's skin.

In a modification to the FIG. 10 system for these purposes, the handpiece 1002 will contain a flashlamp (e.g. which may be the same flashlamp 12 described above), and a filter designed to provide a range of filtering for removal of pigmented and vascular lesions. In a preferred embodiment, the filter (which would correspond to filter 40 discussed above) of this modified version of handpiece 1002, operates to pass wavelengths above about 500 nm and to block wavelengths below about 500 nm. In one embodiment, a 520 nm cutoff filter is used. Alternatively, the flashlamp might instead use a narrower wavelength band within that range (e.g. 500-635 nm or any other sub-band within the 500-1100 nm range).

The absorption peaks for hemoglobin in blood and vascular tissue are located between 500 and 595 nm. Thus, in contrast with the previous discussion of FIG. 10 where wavelengths in the range absorbable by hemoglobin were preferably avoided, the filter used in this modification to the FIG. 10 embodiment allows light transmission in the ranges at which hemoglobin and melanin absorption will occur.

In this embodiment, the reflector within handpiece 12 is preferably constructed of polished aluminum having interior wall surfaces plated with reflective silver. A transparent protective coating covers the silver. Silver is preferred for its ability to most efficiently reflect light across the range of wavelengths at which optimal treatment benefits are achieved (approximately 500-635 nm) for treatment of pigmented and vascular lesions. However, in alternative embodiments the interior wall surfaces of the reflective housing may be formed of other materials such as gold or polished aluminum.

The system is operable in two or more modes, allowing the user to select a mode most suitable for the procedure. For example, the different display buttons shown as A, B and C are implemented for controlling the operation of the flashlamp and sapphire cooling tip temperature to provide different treatments depending on the types of lesions to be removed, e.g. button A for vascular lesions, button C for pigmented lesions, and button B for treating regions having a combination of the two types of lesions.

Each mode produces EMR having a different spectral make-up than that produced using the other modes. To control the spectral output for any given mode, the lamp is run at a constant current density (which equates to a fixed output power) that will produce the desired spectral output. For example, where treatment is desired for vascular lesions such as facial telangiectasia or diffuse redness, a user can select button A on the user interface. In response to this selection, the power supply of the system drives the flashlamp at a high current density (compared to that used with the B and C modes), so as to produce light having a spectral output that is more concentrated in the green to yellow wavelength ranges. In conjunction, the tip temperature is cooled down to 5 degrees C. to protect the epidermis while the vascular lesion at some depth is treated. The system is programmed so that the current density used for the A mode causes the distribution of the spectral output to have a mean in the range of 530-580 nm, where absorption by hemoglobin is the highest. The actual applied current density will vary depending on the design of the GDL.

When treatment is desired for pigmented lesions, the user could press the button C on the user interface 1008, and the power supply would then drive the flashlamp using a lower current density. This lower current density causes the GDL to output therapeutic EMR having a greater component of the output energy at longer wavelengths, so as to avoid strong absorption by hemoglobin in blood and vascular tissue while heating the melanin of the skin. For other applications, such as for regions of skin having both pigmented and vascular lesions, the B button on the interface 1008 will provide for an intermediate current density being applied to the flashlamp. The mean of the corresponding spectral output distribution will lie between the means of the distributions output when buttons A or C are selected.

Figure 21:
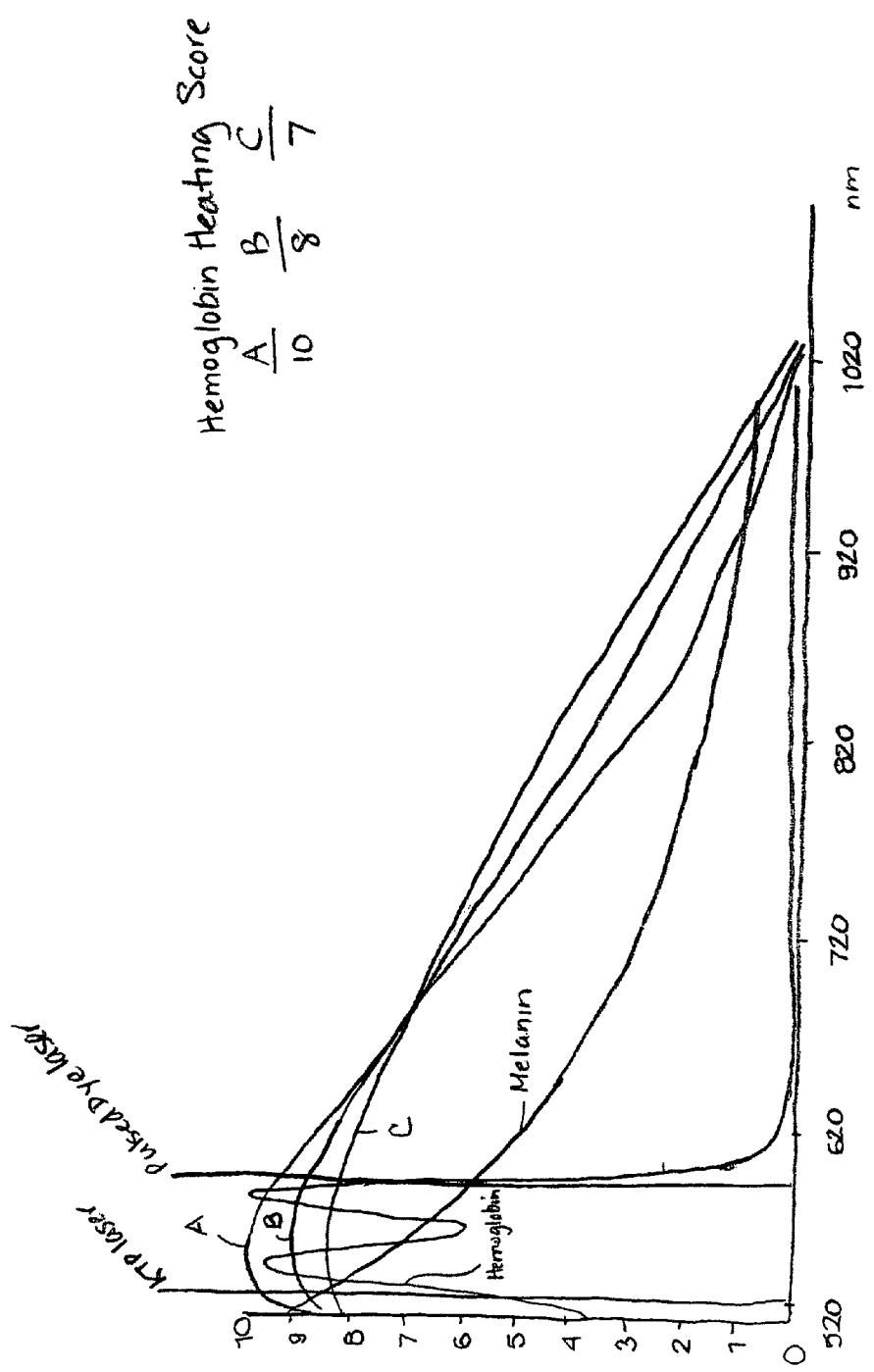
FIG. 21 schematically illustrates the spectral output from a handpiece of an embodiment herein when driven in A, B and C modes for treatment of lesions, and further shows the spectral absorption curves for hemoglobin and melanin.

As illustrated in FIG. 21, because the absorption of hemoglobin within the 500-595 nm range is a very steep function, the spectral shift between modes A, B and C has a very significant effect. In other words, the amount of energy absorbed by hemoglobin and vascular tissue is far less in the B and C modes than in the A modes. This is reflected in the hemoglobin heating scores (defined as the integrated spectral output multiplied by the hemogloblin absorption) shown on FIG. 21, in which the heating scores for A, B and C mode are shown as 10, 8 and 7 respectively. However, given the more gradual fall-off of the absorption curve for melanin, a shift in the spectrum towards longer wavelengths will somewhat, but not dramatically, reduce the melanin absorption.

Other factors influencing the spectral output of the lamp in a given mode include spectral shifting characteristics of the flashlamp, and power supply control of the output lamp current, voltage, pulse duration and pulse shape. Moreover, users of the system might select modes of operation based on the amount of pigmentation in a patient's skin. For example, a user might choose to treat a patient having vascular lesions and heavily pigmented skin using the C mode, with a cold (e.g. 5 C) treatment tip and cooling gel, so as to minimize skin lightening during treatment.

Figure 22:
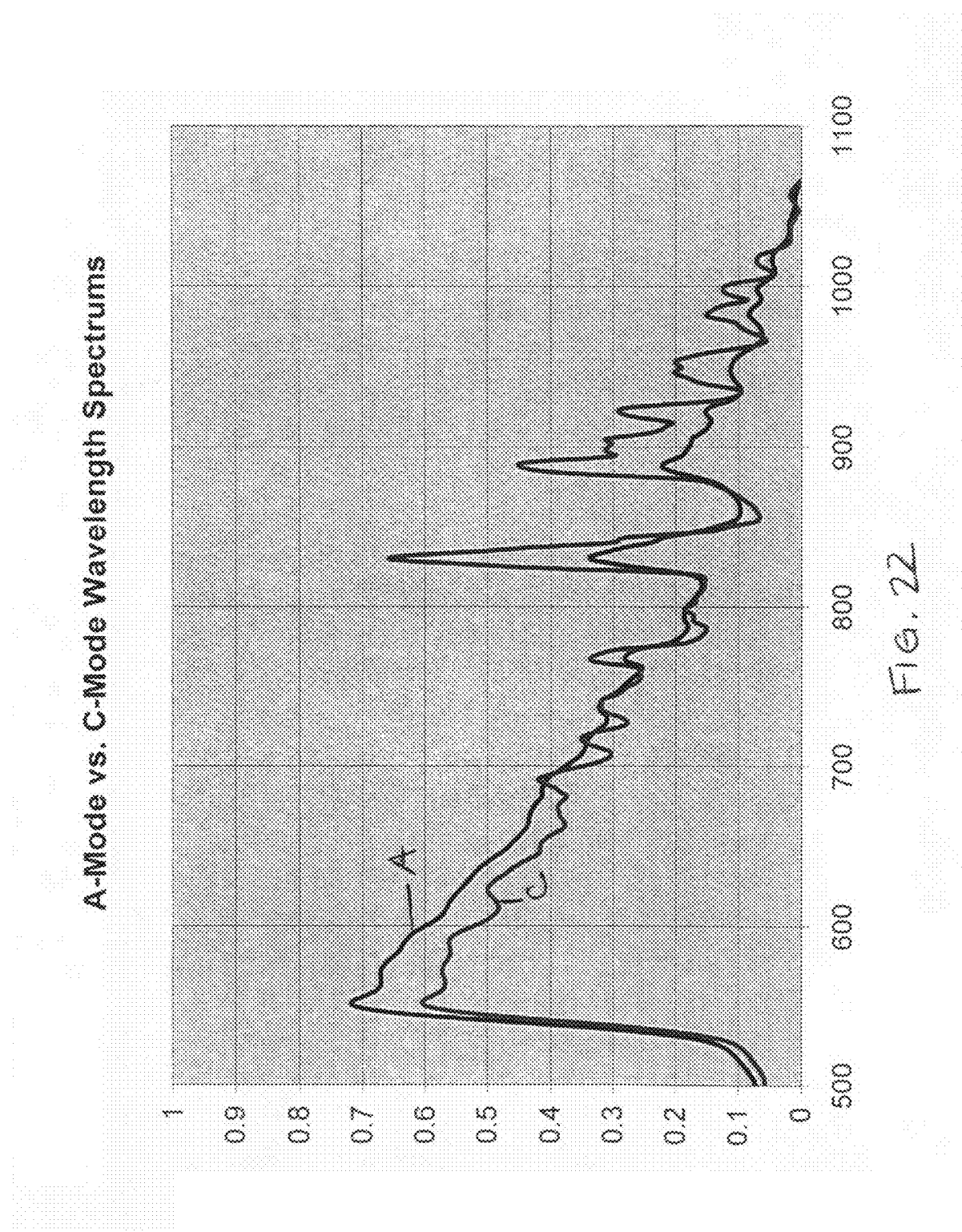
FIG. 22 shows a plot of the spectral output from an experimental handpiece run in A and C modes for treatment of lesions.

FIG. 22 also shows the wavelength spectrums for A and C mode, based on actual test data using the Limelight(™) system available from Cutera, Inc. of Brisbane, Calif., the features of which are incorporated herein by reference.

The FIG. 10 system can optionally allow the user to input a selected pulse width for the therapeutic EMR being applied to an area of tissue being treated, allowing for independent control and variation of pulse width, the amount of fluence, and the spectral output (by controlling the current density through the lamp).

In one embodiment where a user inputs A (corresponding to vascular lesions), the pulse width can be in the range of approximately 2 to 13 ms, depending on the selected fluence, which may be in the range of 5-30 J/cm$^2$. The system in this mode delivers a peak power of approximately 7000 W. The thermoelectric cooler preferably operates to significantly cool the sapphire contact surface temperature (e.g. approximately 5 C) to minimize superficial tissue damage while allowing penetration of the photons to the vascular lesions, generally 1-1.5 mm below the skin surface. A cooling gel may be applied to skin to assist in cooling and to provide optical index matching between the skin and the contact surface.

Where input C is selected the pulse width can be in the range of 10 to 60 ms, and fluence can be in a range of 5-30 J/cm$^2$ with a peak power of approximately 1500 W. C mode operation uses less contact surface cooling (e.g. to approximately 10-20 C) so as to allow heating of the very superficial pigmented lesions to occur.

Parameters for B mode may include pulse widths in the range of 4 to 30 ms seconds, fluence level in the range of 5-30 J/cm$^2$, peak power of approximately 3000 W, and skin cooling targeted to 5 C.

In use of the FIG. 10 system to treat lesions, the FIG. 18 power supply will function in a manner similar to that described in connection with its use for hair removal treatments. More specifically, a signal 1804 based on the selection made by the user based on the type of skin lesions to be treated is input to the controller 1802, and the switch is operated to provide for relatively wide range of current densities to the lamp. For example in one embodiment where a user inputs C (for pigmented lesions) on the user interface, the controller may refer to a look-up table, or be otherwise programmed to drive the switch of the power supply to output a lower current from the power supply to the lamp, and thus a lower current density through the lamp, than in a situation where a user inputs A on the user interface, indicating vascular lesions.

The method 1900 illustrated in the flow diagram of FIG. 19 is likewise representative of a method for treatment of vascular and pigmented lesions. Initially, a user will observe an area of skin where a lesion is to be removed. The user will make a determination 1902 as to whether the lesion(s) is/are vascular lesions, pigmented lesions, or a combination of the two. Based on the user's determination regarding the area to be treated, the user inputs 1904 a selection through the user interface of the system (this could for example correspond to the A, B, and C selections shown in FIG. 10). Based on the user input the controller makes a determination 1906 regarding the current density which should be transmitted through the flashlamp, and this current density will correspond to a desired spectral output by the flashlamp. In one embodiment in addition to inputting 1904 a determination regarding the area of skin to be treated, the user can also select 1908 and input 1910 an amount of fluence to be provided to area of skin being treated. Additionally, a user could also be provided with the ability to select an effective pulse width of the therapeutic EMR to be applied to the area of tissue. Based on the user input selections, the controller makes a determination 1912 as to time durations for incremental pulses, and time durations for intervals between incremental pulses, to produce a desired fluence.

The user positions the contact surface of the handpiece in contact with the skin that is to be treated and depresses the footswitch. Based on the user inputs, and the subsequent determinations made by the controller, the controller controls 1914 the power supply to drive 1916 the flashlamp, and the resulting therapeutic EMR output is applied 1918 to the area of skin to be treated.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

Any and all patents, patent applications and printed publications referred to above are incorporated by reference.

We claim:

1. A dermatological treatment method, comprising:
   identifying a type of dermatological lesion in an area of skin to be treated;
   driving a gas discharge lamp with a first current density such that the gas discharge lamp outputs a first therapeutic electromagnetic radiation which has a first spectral profile, when the area of skin is determined to have a vascular lesion;
   driving the gas discharge lamp with a second current density such that the gas discharge lamp outputs a second therapeutic electromagnetic radiation which has a second spectral profile, when the area of skin is determined to have a pigmented lesion, wherein the first current density is higher than the second current density so that the second spectral profile has more energy distributed at longer wavelengths than the first spectral profile; and
   selectively transmitting said first and second therapeutic electromagnetic radiation outputs from the gas discharge lamp through a cooled window that is in contact with the area of skin to be treated, and wherein when said first therapeutic electromagnetic radiation output is being transmitted, the window is cooled to a temperature of 5 degrees centigrade and wherein when said second therapeutic electromagnetic radiation output is being transmitted, the window is cooled to temperature between 10 and 20 degrees centigrade.

2. The dermatological treatment method of claim 1, wherein the first spectral profile has a mean within the spectral range of 500-595 nm.

3. The method of claim 1, further including:
   transmitting one of the first or second therapeutic electromagnetic radiation outputs from the gas discharge lamp through a filter that blocks electromagnetic radiation below 500 nm.

4. The method of claim 3 wherein the filter blocks one of the first or second therapeutic electromagnetic radiation outputs below 520 nm.

* * * * *